(12) United States Patent
Kallenbach et al.

(10) Patent No.: US 11,344,717 B2
(45) Date of Patent: May 31, 2022

(54) OUTLET GRAFT FOR A BLOOD PUMP AND SYSTEM

(71) Applicant: Berlin Heart GmbH, Berlin (DE)

(72) Inventors: Sebastian Kallenbach, Kassel (DE); Daniel Phillips, Berlin (DE)

(73) Assignee: BERLIN HEART GMBH, Berlin (DE)

( * ) Notice: Subject to any disclaimer, the term of this patent is extended or adjusted under 35 U.S.C. 154(b) by 293 days.

(21) Appl. No.: 16/075,566

(22) PCT Filed: Feb. 3, 2017

(86) PCT No.: PCT/EP2017/052348
§ 371 (c)(1),
(2) Date: Aug. 3, 2018

(87) PCT Pub. No.: WO2017/134204
PCT Pub. Date: Aug. 10, 2017

(65) Prior Publication Data
US 2019/0046701 A1    Feb. 14, 2019

(30) Foreign Application Priority Data

Feb. 4, 2016   (EP) .................................... 16154223

(51) Int. Cl.
*A61M 1/36*      (2006.01)
*A61M 60/857*    (2021.01)
(Continued)

(52) U.S. Cl.
CPC ........ *A61M 60/857* (2021.01); *A61M 1/3659* (2014.02); *A61F 2/07* (2013.01); *A61M 25/0108* (2013.01); *A61M 2205/32* (2013.01)

(58) Field of Classification Search
CPC . A61F 2/064; A61F 2/07; A61L 31/18; A61B 17/0218; A61M 1/1008; A61M 1/3659; A61M 25/0108; A61M 2205/32
See application file for complete search history.

(56) References Cited

U.S. PATENT DOCUMENTS

| 8,535,370 B1 * | 9/2013 | Eckert ....................... A61F 2/07 |
| | | 623/1.13 |
| 2002/0095210 A1 * | 7/2002 | Finnegan ................ A61F 2/064 |
| | | 623/3.26 |

(Continued)

FOREIGN PATENT DOCUMENTS

WO    WO 2015/109328 A2    7/2015

OTHER PUBLICATIONS

International Search Report issued in International Application No. PCT/EP2017/052348, dated Apr. 24, 2017, pp. 1-5, European Patent Office, Rijswijk, The Netherlands.

*Primary Examiner* — Ankit D Tejani
*Assistant Examiner* — Joshua Brendon Solomon
(74) *Attorney, Agent, or Firm* — Crowell & Moring LLP

(57) ABSTRACT

The present application relates to an outlet graft for a blood pump as well as to a system comprising a blood pump and an outlet graft that is connected to an outlet of the blood pump. The outlet graft includes a first end opposite a second end such that a longitudinal axis is formed between the first and second ends. The second end is connectable to a blood vessel and a lumen with a closed cover. A first strip included in the cover extends parallel to the longitudinal axis and is made of a material that is of a higher contrast under x-rays than the cover.

13 Claims, 8 Drawing Sheets

(51) Int. Cl.
*A61M 25/01* (2006.01)
*A61F 2/07* (2013.01)

(56) References Cited

U.S. PATENT DOCUMENTS

| | | | |
|---|---|---|---|
| 2006/0253190 A1* | 11/2006 | Kuo | A61F 2/07 623/1.44 |
| 2009/0171436 A1* | 7/2009 | Casanova | A61L 31/18 623/1.13 |
| 2011/0160517 A1 | 6/2011 | Smith et al. | |
| 2012/0116503 A1* | 5/2012 | Grewe | A61F 2/07 623/1.46 |
| 2012/0142995 A1 | 6/2012 | Tao et al. | |
| 2014/0005467 A1 | 1/2014 | Farnan et al. | |
| 2015/0290370 A1* | 10/2015 | Crunkleton | A61B 17/0218 600/16 |
| 2017/0319359 A1* | 11/2017 | Mehta | A61F 2/07 |

\* cited by examiner

OUTLET GRAFT FOR A BLOOD PUMP AND SYSTEM

CROSS-REFERENCE TO RELATED APPLICATIONS

This application is a 371 nationalization of international patent application PCT/EP2017/052348 filed Feb. 3, 2017, which claims priority under 35 USC § 119 to European patent application 16154223.8, filed Feb. 4, 2016. The entire contents of the above-identified application are hereby incorporated by reference.

TECHNICAL FIELD

The present disclosure relates to an outlet graft for a blood pump and to a system comprising an outlet graft.

DETAILED DESCRIPTION

Figure 1:
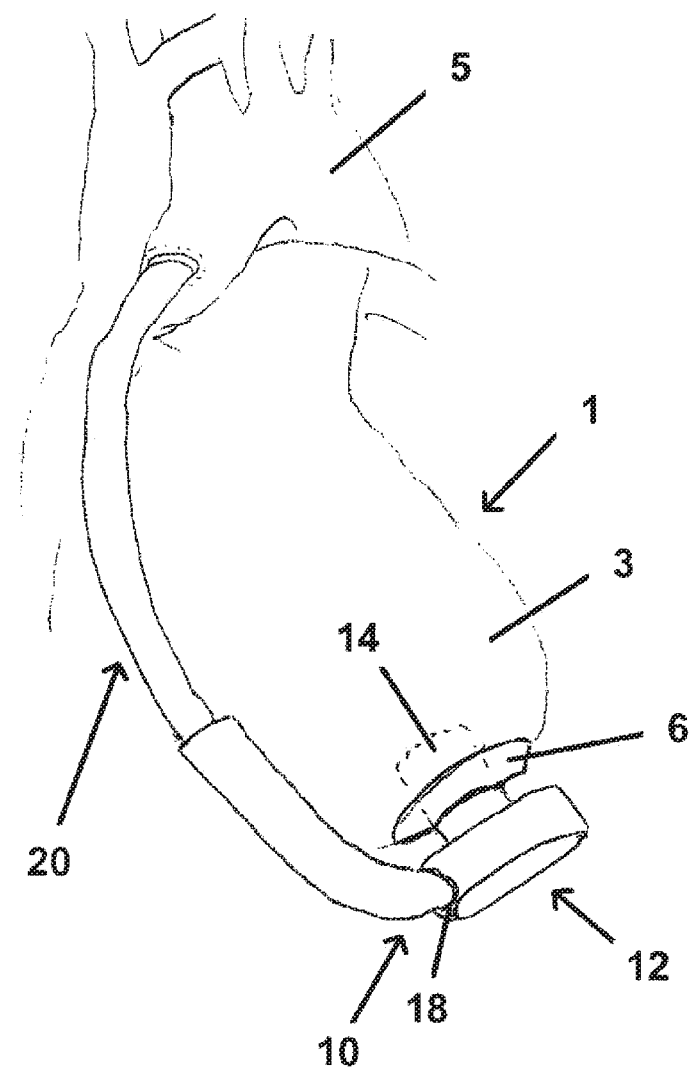
FIG. 1 shows a schematic system according to this application.

Heart assist pumps, such as ventricular assist devices (VADs), are known in the prior art. In addition, there are numerous proposals for connecting pumps of this kind to an organ, for example to a heart.

A large number of VAD connector systems comprise on the one hand a connector which for example is anchored at an apex of a left ventricle, for example with the aid of a suture. An opening is then cut into the ventricle, through which opening the blood pump can be inserted into the ventricle or a cannula is attached to the connector, which cannula, at its end not attached to the heart, is connected to a connector of the blood pump.

In order to achieve a secure attachment between the outlet of the blood pump and a blood vessel, for example the aorta or the subclavian artery, substantially rigid cannulas are often provided in the prior art.

The rigid cannulas have very good flow properties for blood. However, due to their rigidity, the cannulas can be connected to the pump and the blood vessel only with difficulty if the thorax is not opened over a large area, and the cannula cannot be inserted under the visual control of a doctor.

In order to ensure improved workability here, even for the case of minimally invasive implantation techniques, i.e. implantation techniques which do not require the thorax to be opened over its entire area, use is being made increasingly of what are known as graft materials. These graft materials for example can comprise a fluid-tight textile layer, which defines the lumen through which the blood is conveyed.

A disadvantage of theses grafts, however, is their low rigidity, which can easily result in torsion, bending, or constriction of the graft lumen and therefore a reduced blood flow.

The outlet graft and system provides a remedy for this.

The outlet graft in one embodiment comprises a first end and an opposite end thereto, wherein the first end can be connected to a blood pump, for example an axial or radial pump, and the opposite end can be connected to a blood vessel, for example the aorta or a subclavian artery. A lumen with a closed cover is formed between these two ends, wherein the lumen extends substantially along a longitudinal axis. Here, the cover of the outlet graft is preferably flexible.

The cover comprises a first strip running parallel to the longitudinal axis, wherein the first strip consists of a material that is of a higher contrast under x-rays than the cover. Alternatively, the material of the first strip can also be of a higher contrast than the cover under other imaging methods; other imaging methods of this kind are for example ultrasound or magnetic resonance imaging methods.

When implanting an outlet graft of this kind, it is possible to determine on the basis of the first strip running parallel to the longitudinal axis, by means of an imaging source, such as an x-ray source, whether the first end, which is to be attached to a blood pump, and the opposite end, which is to be connected to the blood vessel, is/are twisted. Since a twisting or rotation or torsion of the outlet graft is to be prevented, it is possible to view on a screen, once the outlet graft has been attached for example to the blood vessel, whether the first strip follows substantially merely the course of the longitudinal axis. If, however, a twisting or rotation of the outlet graft can be identified on the screen, said outlet graft can be oriented in such a way that it can be untwisted prior to being connected to the blood pump (or prior to the opposite end being connected), thus providing a large-volume and fold-free outlet that is more satisfactory for the outlet of the blood pump. In this way, the pump capacity of the connected blood pump is improved.

In a further embodiment the cover comprises a second strip, running parallel to the longitudinal axis, made of a material of a higher contrast under x-rays than the cover. Here, the second strip is spaced apart from the first strip. The spacing is selected preferably in such a way that the distance is an angular segment of exactly 180° or less than 180°, preferably less than 90°, but more than 10°. In this way, the first and second strips can be perceived easily as being separate from one another on a screen under x-ray irradiation, and twists or rotations can be noticed more easily.

In a further embodiment the cover comprises a third strip that runs helically around the cover in the direction of the longitudinal axis, and that is made of a material that is of a higher contrast under x-rays than the cover. Since the helix has a predetermined pitch, a change in the pitch can be observed in the event of a twisting or rotation of the outlet graft. The change in the pitch can be used as an indicator or measure for a twisting or rotation and for the untwisting.

Here, the helix can run around the cover in a clockwise or anticlockwise direction. The fact of whether the outlet graft or the third strip runs around the cover in a clockwise or anticlockwise direction can be made dependent on whether the outlet graft is connected to a blood pump which has been used in the left or right ventricle.

In a further variant the material of the cover of the outlet graft can comprise a polymeric material or can consist of a polymeric material, in specific exemplary embodiments PTFE. Further polymeric materials are for example PE, PP, PET, PVC, PC, PMMA, PUR, polysiloxane, PEEK, PSU or PHEMA and mixtures of the aforementioned polymeric materials.

In a further variant the outlet graft is formed in such a way that the cover is helically surrounded and reinforced by a plastics material strip. Here, the plastics material strip can have a very small pitch, such that two adjacent revolutions along the longitudinal axis are distanced from one another for example by less than 0.5 cm, preferably less than 0.3 cm. The use of the plastics material strip reinforces the graft and makes it more dimensionally stable with respect to an external pressure.

In a further embodiment the first end of the outlet graft is provided with a connector for connection to the blood pump. Here, the connector can have an extension extending in the direction of the opposite end of the outlet graft. Here, the extension is selected from a material that is of a greater contrast under x-rays compared to the material of the cover. In this way, it is possible to determine whether the outlet graft or cover thereof is twisted relative to the connector. In further embodiments the connector can have more than one extension, for example two extensions spaced apart from one another. The extension is preferably formed in such a way that it overlaps with the first strip and forms an extension of the strip. The extension in some embodiments can be formed in a strip-shaped manner, for example. In this way, deviations or twists or rotations between the first strip and the extension can be determined in a simple way. The extension can thus be used as a reference for a twisting or rotation of the cover.

In a further embodiment the outlet graft comprises a protective element at least partially encasing the cover. Here, it is provided in a variant that the protective element extends from the first end, which can be connected or is connected to the blood pump, towards the opposite end, but not over the entire circumference of the cover. This means that the protective element surrounds merely a portion from the first end to a point distanced from the opposite end. A reinforcement of the graft in the vicinity of the pump is produced by means of the encasing protective element.

Here, it can be provided in a variant that the protective element comprises a marking that is visible under x-ray irradiation. The visible marking can also in turn be used as a reference for a twisting or rotation of the cover. In a variant the visible marking is oriented parallel to the longitudinal axis of the cover, preferably in the form of a strip. Alternatively, the visible marking can be formed helically, coaxially with the first strip of the cover, or linearly spaced apart from the first strip. A twisting or rotation is hereby identified in a simple way.

In a further embodiment the cover comprises an endoskeleton and/or exoskeleton, preferably made of a shape-memory material, such as nitinol. The endoskeleton or exoskeleton offers an additional reinforcement of the outlet graft. Certain portions of the outlet graft can also be pre-shaped, that is to say the shape-memory material can predefine bends for example, such that a twisting or rotation can be avoided in a particularly reliable manner. Here, the cover can surround the endoskeleton or can be embedded in the exoskeleton.

The outlet graft is preferably used in conjunction with a blood pump, such as an axial or radial pump.

A system of this kind is suitable for example for preventing a twisting or rotation of the outlet graft during implantation of the blood pump, in particular in the case of hidden implantation of the blood pump within the scope of a minimally invasive implantation, and can thus bring about an improved pump capacity.

The outlet graft will be described in greater detail hereinafter with reference to a number of exemplary embodiments.

In the drawings

Figure 2:
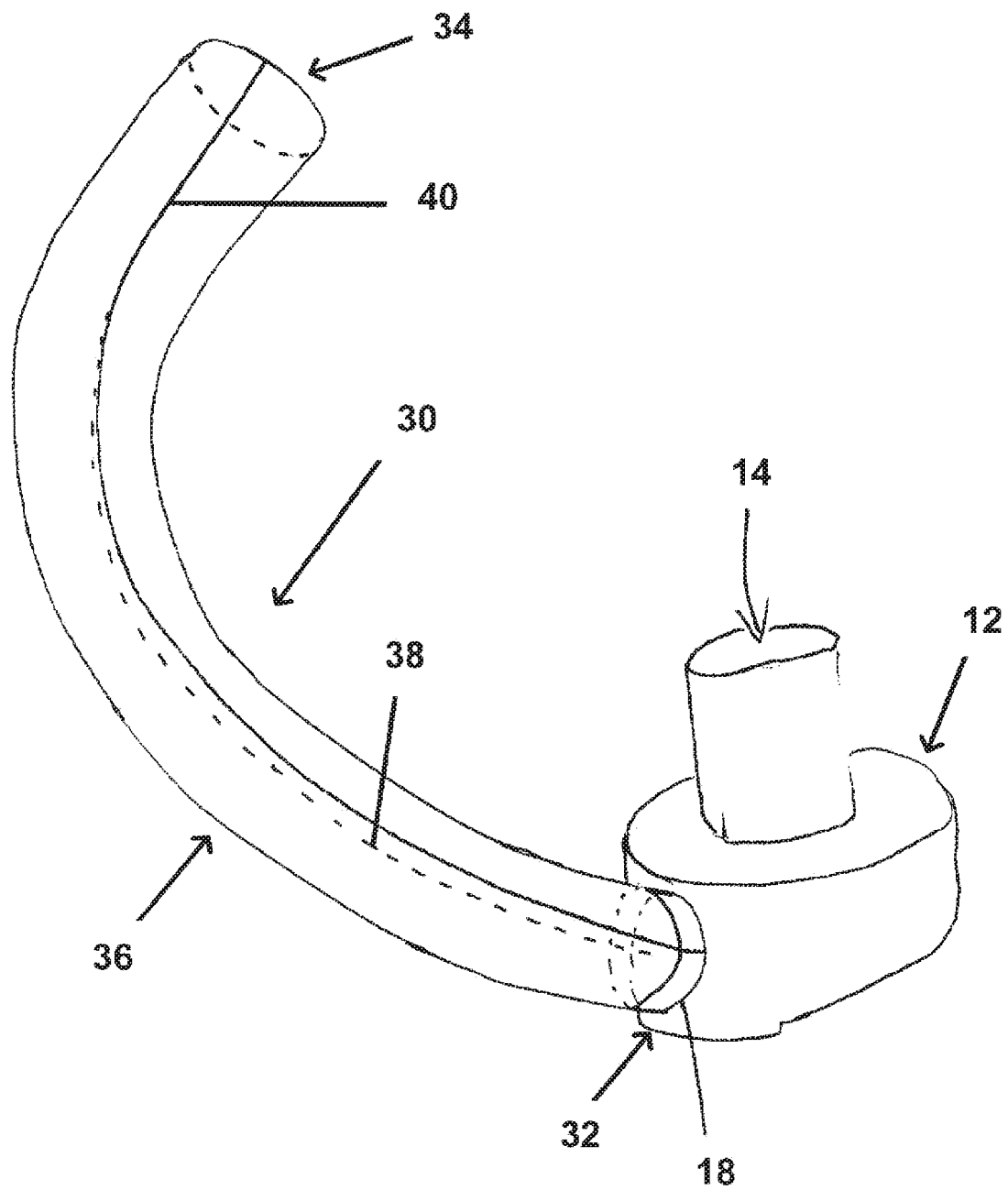
FIG. 2 shows a further schematic system according to this application.
Figure 3A:
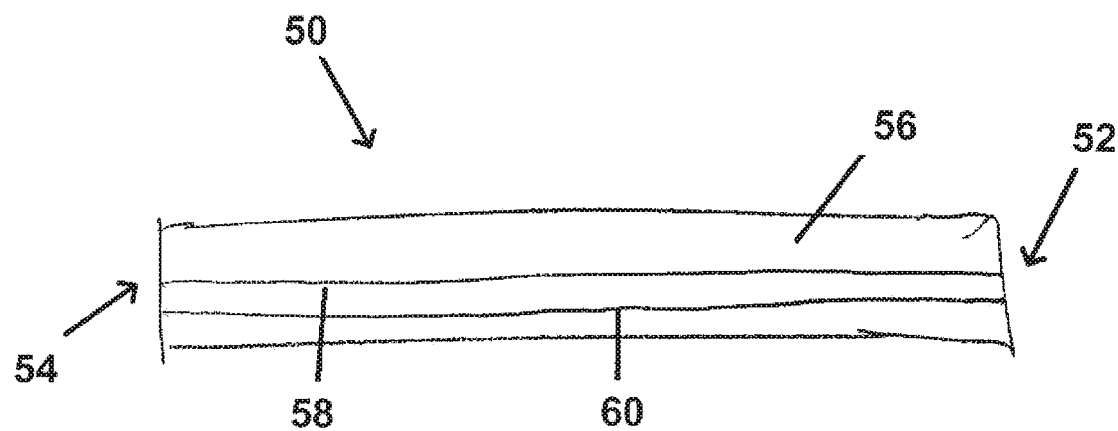
FIGS. 3a to 3c show embodiments of an outlet graft.
Figure 3B:
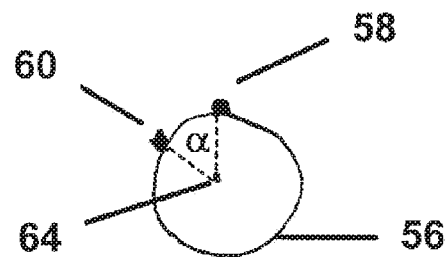
Figure 3C:
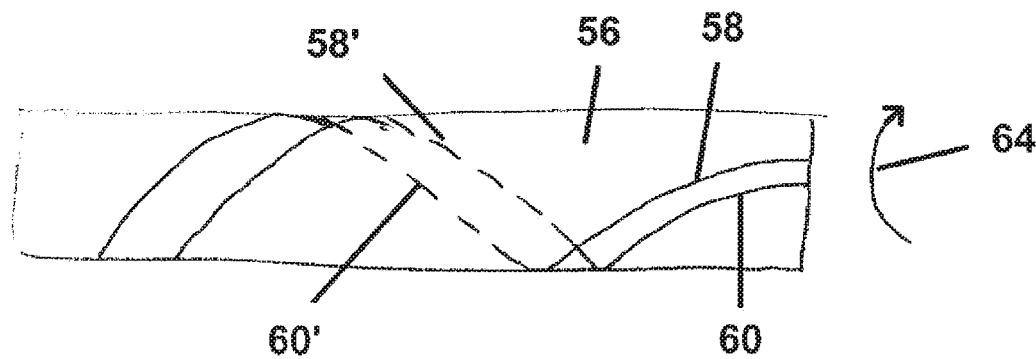
Figure 4A:
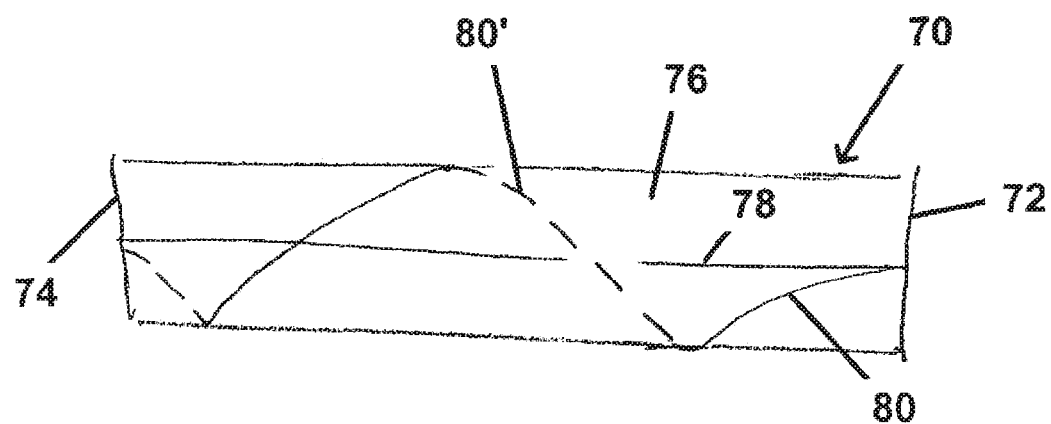
FIGS. 4a and 4b show further embodiments of an outlet graft.
Figure 4B:
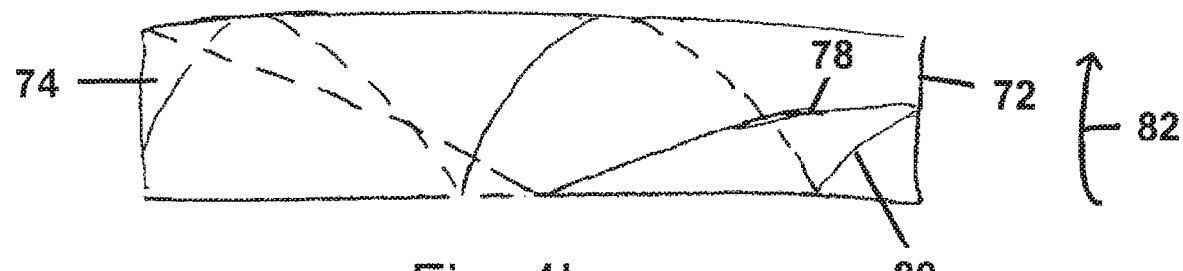
Figure 5A:
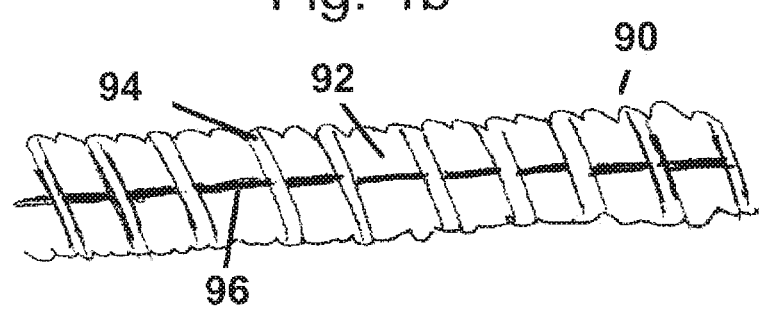
FIGS. 5a and 5b show further embodiments of an outlet graft.
Figure 5B:
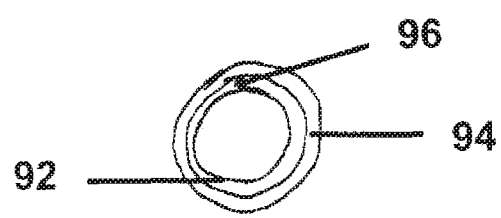
Figure 6A:
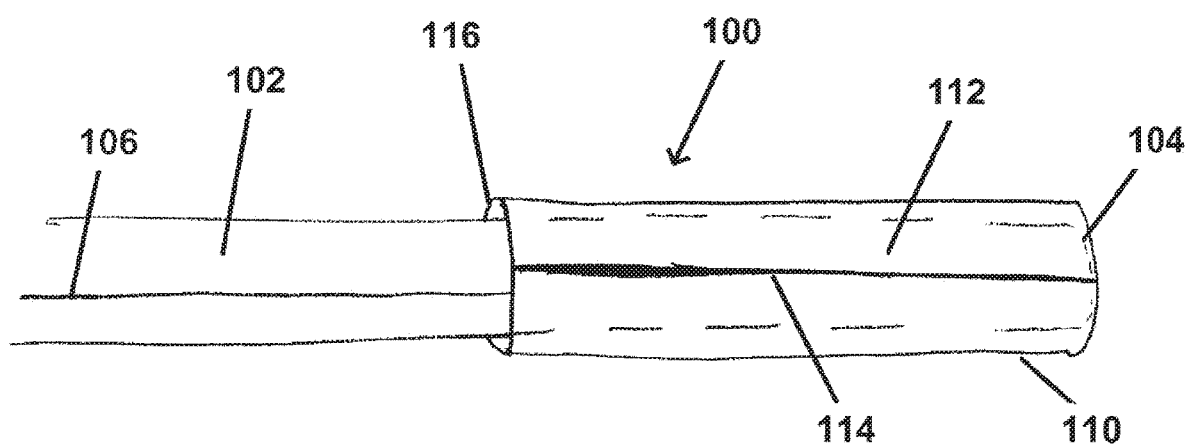
FIGS. 6a and 6b show embodiments of an outlet graft with protective element.
Figure 6B:
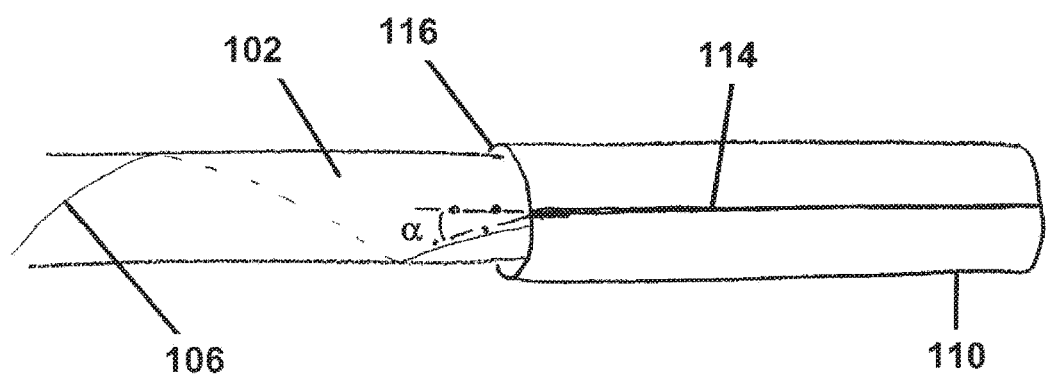
Figure 7A:
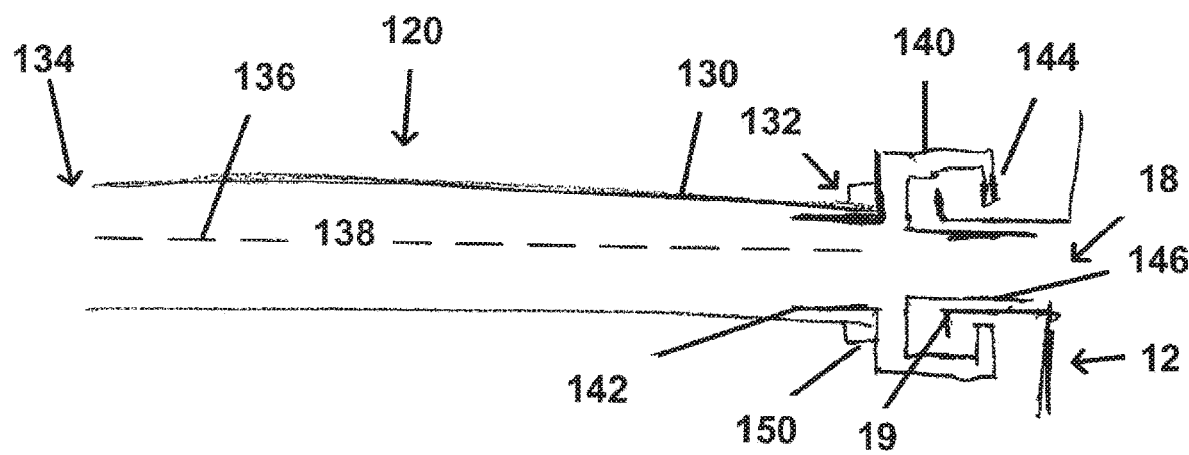
FIGS. 7a to 7c show an outlet graft with a connector.
Figure 7B:
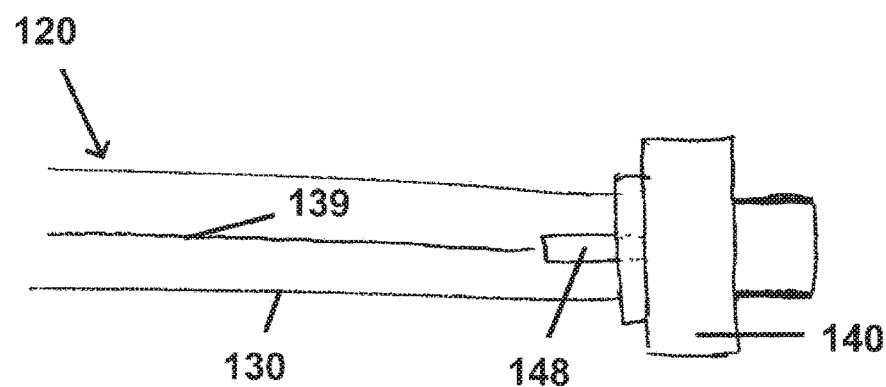
Figure 7C:
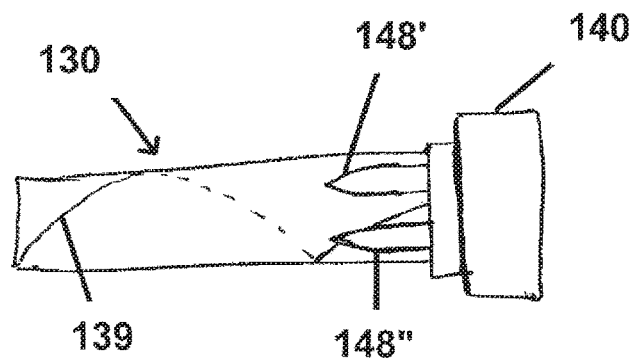
Figure 9:
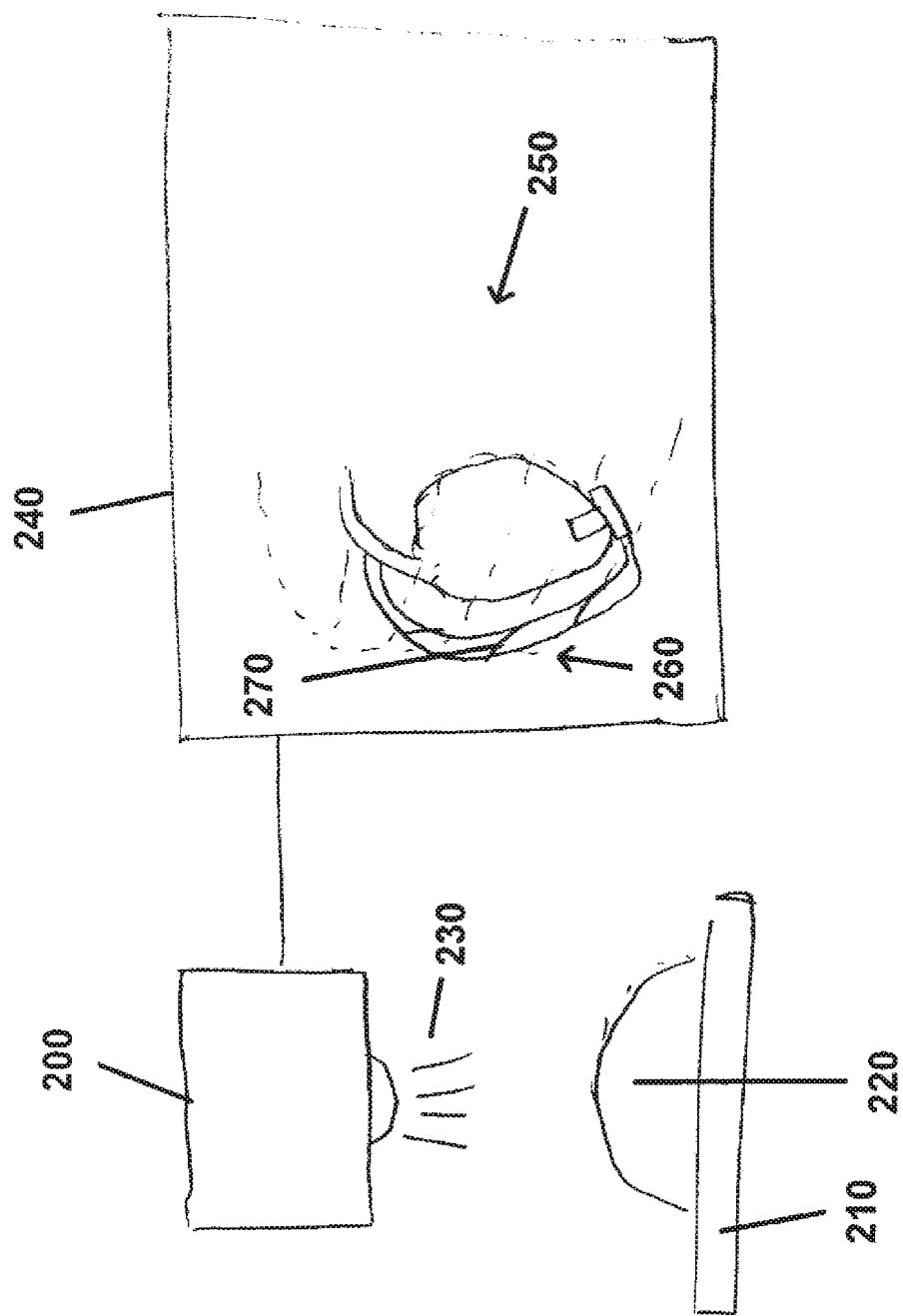
FIG. 9 shows a schematic depiction of the use of an outlet graft during an implantation procedure.

FIG. 1 shows a schematic system according to this application;

FIG. 2 shows a further schematic system according to this application;

FIGS. 3a to 3c show embodiments of an outlet graft;

FIGS. 4a and 4b show further embodiments of an outlet graft;

FIGS. 5a and 5b show further embodiments of an outlet graft;

FIGS. 6a and 6b show embodiments of an outlet graft with protective element;

FIGS. 7a to 7c show an outlet graft with a connector;

FIGS. 8a to 8d show an outlet graft with an endoskeleton and exoskeleton;

FIG. 9 shows a schematic depiction of the use of an outlet graft during an implantation procedure.

FIG. 1 shows a schematic depiction of a heart 1 and of the left ventricle 3 and aorta 5 thereof. A ventricular assist system (VAD) 10 has been inserted in the heart and comprises a blood pump 12, inter alia.

The blood pump 12 is introduced via its inlet 14 into the apex of the left ventricle 3. The blood pump 12 is fixed to the heart by means of a suture ring 16. The blood pump 12 also comprises an outlet 18, which is guided to the aorta 5 by means of an outlet graft 20, wherein the end of the outlet graft 20 opposite the outlet 18 is sewn to the aorta, such that blood from the left ventricle can be conveyed into the aorta 5, bypassing the aortic valve. The blood pump 12 and the outlet graft 20 together form a system which for example can be used in the case of the minimally invasive implantation of the VAD 10. Amongst other things, aspects of various outlet grafts according to the application will be explained in the following figures.

FIG. 2 schematically depicts an outlet graft 30, which comprises a first end 32, which is connected to an outlet of the blood pump 12. Here, the first end can be fixed to the blood pump by an attachment means, for example a clip, a cable tie, or a connector (not shown in greater detail). Opposite the first end 32, there is a further end 34, which can be connected to the blood vessel, for example the aorta or the subclavian artery. The outlet graft 30 can be directly sewn to the aorta, such that the blood can flow through the outlet graft 30 into the aorta. The outlet graft 30 has a tube shape 36, wherein the tube delimits a lumen formed between the first and second end. The cover defining the lumen can be formed for example from a plastics material, such as PTFE. Furthermore, coated textiles which enable biocompatible ingrowth of the graft are also envisaged.

A first strip 40 running parallel to the longitudinal axis 38 of the tube 36 is located on an outer side of the cover. Whereas the material of the tube 36 generates only a small amount of contrast on an x-ray image, the first strip 40 can be manufactured for example from a metal which generates a high contrast under x-rays. In this way, the orientation of the outlet graft can be made visible by means of x-ray irradiation of the thorax, even in the event that the graft is inserted within the scope of a minimally invasive operation, i.e. in an operation in which it is not possible to have direct visual contact with the graft already located in the body. Since the strip runs parallel to the longitudinal axis in the untwisted state, any twisting, i.e. a rotation of the first end 32 relative to the second end 34 about the longitudinal axis 38, can be quickly identified. The twisting or rotation is visible here for example in the form of a curving of the first strip 40. In order to create a particularly large volume which is available for the blood flow, an outlet graft that is connected in a twist-free manner both to the pump and the blood vessel is advantageous. The twist-free insertion of the graft during the course of a minimally invasive operation can be ensured by means of the first strip 40 and monitoring thereof under x-rays.

A further embodiment of an outlet graft is depicted in FIGS. 3a to 3c. The outlet graft 50 extends between the first end 52 and a second end 54. A first strip 58 running parallel to the longitudinal axis and a further, second strip 60 are attached to the cover 56, wherein both strips are made of the same material. In other variants the strips can be made of different materials. The two strips are parallel to one another and are spaced apart from one another. As can be seen in FIG. 3b, the first strip 58 has an angular spacing from the second strip 60 of approximately α=45°. In an x-ray image or computerised tomography scan, the first and second strips 58 and 60 are visible in the untwisted state, as is shown by way of example in FIG. 3a, as lines running parallel to one another. If the first end is now twisted relative to the second end in a direction of rotation 64, the connected strips 58 and 60 (connected fixedly to the cover 56) are also rotated accordingly. Here, the lines running parallel to one another are visible in the form of a curve. The portions of the strips 58 and 60 depicted in the form of solid lines in FIG. 3c are portions located on the upper side of the cover, and the portions 58' and 60' depicted as dashed lines, as considered from the perspective of FIG. 3c, are located on the rear side of the cover 56. Due to the change in the course of the strips, it is discernible during an imaging method that the outlet graft 50 has rotated. Here, the angular distance between the first and second strips 58 and 60 can be freely selected. However, distances of less than 180° are preferred in order to break a rotational symmetry in the cross-section of the outlet graft.

A further variant of an outlet graft is depicted in FIGS. 4a and 4b. The outlet graft 70 comprises a first end 72 and a second end 74 and a cover 76. In the shown exemplary embodiment the cover comprises a first strip 78, which extends parallel to the longitudinal axis of the outlet graft 70. A second strip 80 is also shown, which winds helically around the cover 76, which is illustrated on the basis of the solid line and the dashed portion depicted by 80'. Here, the strip 80 running helically around the cover runs from the first end to the second end, as considered in a clockwise direction. In the event of a twisting or rotation of the first end 72 relative to the second end 74 in the direction 82, the course of the first strip 78 and of the second strip 80 changes, such that a twisting or rotation is visible on the basis of the different geometry of the courses of the strips, even within the scope of an imaging method.

A further variant of an outlet graft is depicted in FIGS. 5a and 5b. The outlet graft 90 is shown here merely in a portion. This means that the first and second end are not visible. Here, the graft has a cover 92, which is reinforced by a plastics material strip 94 winding in a spiraled manner around the cover. A first strip 96 is also visible, which has a higher contrast than the cover and the plastics material strip. This means that although the strip 96 is partially hidden by the plastics material strip 94 in visible light, the first strip can still be identified as a solid line in an imaging method, such as computerised tomography. This is illustrated once more on the basis of FIG. 5b.

A further variant of an outlet graft is depicted in FIGS. 6a and 6b. The outlet graft 100 comprises a cover 102 surrounding a lumen and having a first end 104 and a second end (not shown). A first strip 106, which runs substantially parallel to the longitudinal axis of the cover, is located in portions on the cover. A protective element 110, which for example can be made of a biocompatible plastics material or a metal, extends from the first end 104 in the direction of the opposite end. Besides a sheathing 112 surrounding the cover, the protective element also has a strip 114, which is of a greater contrast under x-rays compared to the sheathing 112. It can be seen on the basis of FIG. 6a that the strip 114 also runs substantially parallel to the longitudinal axis of the cover 102. However, the strip 106 is offset relative to the strip 114 in the untwisted state. If the cover 102 is now rotated from its first end towards the second end, as depicted in FIG. 7b, this has no effect on the protective element 110, the strip 114 of which still runs substantially parallel to the untwisted longitudinal axis of the cover 102. The first strip 106, however, is twisted and for example at the end 116 of the protective element 110 forms an angle α with the first strip 106 that is greater than 0. The value of the angle can be used for example as a measure for the degree of twisting or rotation.

A further variant of an outlet graft is depicted in FIGS. 7a to 7c. The outlet graft 120 comprises a cover 130, which comprises a first end 132 and an opposite second end 134 and a lumen 138 extending along a longitudinal axis 136. The outlet graft 120 also comprises a connector 140, which for example can be made of titanium or another biocompatible metal. Further metals can be Co alloys, Ti alloys (α+β), Ni alloys, Cr alloys, Ta alloys, or Pt alloys. These metallic materials can also be used in some embodiments as materials for metals mentioned at other points of this application. Alternatively or in combination with the metallic materials, ceramic materials such as $Al_2O_3$, $ZrO_2$ or $TiO_2$ can also be used. The connector 140 in the depicted cross-section shows a first pipe portion 142, which extends from the first end to the second end of the cover 130 and onto which the first end 132 of the cover can be fitted. The connector also comprises a claw ring 144, which can engage behind a collar 19 of the outlet 18 of the blood pump 12. The connector 140 also has a second pipe portion 146, which can be inserted into the outlet 18, such that a fluid-tight connection can be produced between the cover and the blood pump 12. The first and second pipe portion are each optional.

The cover 130 can be connected to the connector for example by means of a cable tie 150. Here, the connector can be connected to the cover already prior to the implantation of the outlet graft, so that the connection of the outlet graft 120 to the blood pump 12 is simplified. in FIG. 7a the outlet graft 120 is shown as it would be seen in an x-ray image. An outer boundary of the cover can be seen. The first strip 139, which runs parallel to the longitudinal axis 136, can also be seen. The connector 140, besides the features already described, also comprises an extension 148, which extends substantially parallel to the longitudinal axis of the cover. Here, the extension 148 and the first strip 139 overlap one another. Here as well, a twisting or rotation of the outlet graft from the first end to the second end of the cover is easily visible in an x-ray image. Although merely a rectangular extension 148 is shown in FIG. 7b, an alternative connector, as depicted for example in FIG. 7c, can comprise a plurality of extensions 148' and 148". A twisting or rotation of the cover 130 is additionally shown in FIG. 7c, wherein it can be seen that the first strip 139 has left its "untwisted" position between the extensions 148' and 148". The extensions can additionally help here to determine whether the connector is firmly fixed relative to the cover or whether it can slip through, provided a fixed orientation of the extensions 148 or 148' and 148" relative to the first strip 139 was selected prior to the implantation of the outlet graft. Although extensions 148 and 148" are shown in the example described here (said extensions protruding further in the direction of the second end of the cover 130 than the first pipe portion 142), the pipe portion 142 in an alternative embodiment can be slotted for example, such that the slot in the metal is merely of a low x-ray contrast. A fixed arrangement relative to one another can also be easily identified in the x-ray image.

Figure 8A:
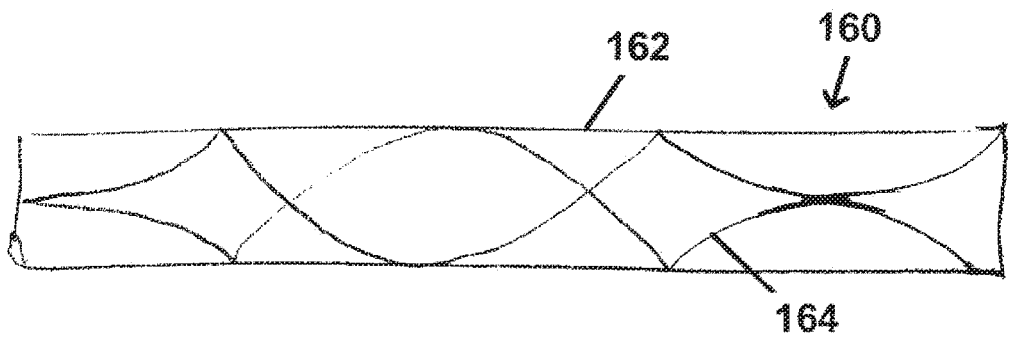
FIGS. 8a to 8d show an outlet graft with an endoskeleton and exoskeleton.
Figure 8B:
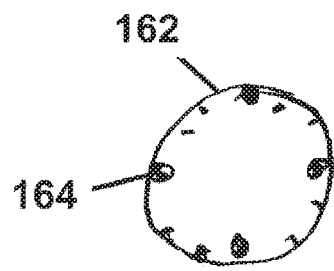
Figure 8C:
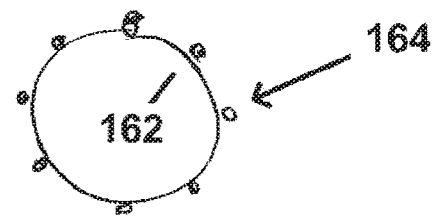
Figure 8D:
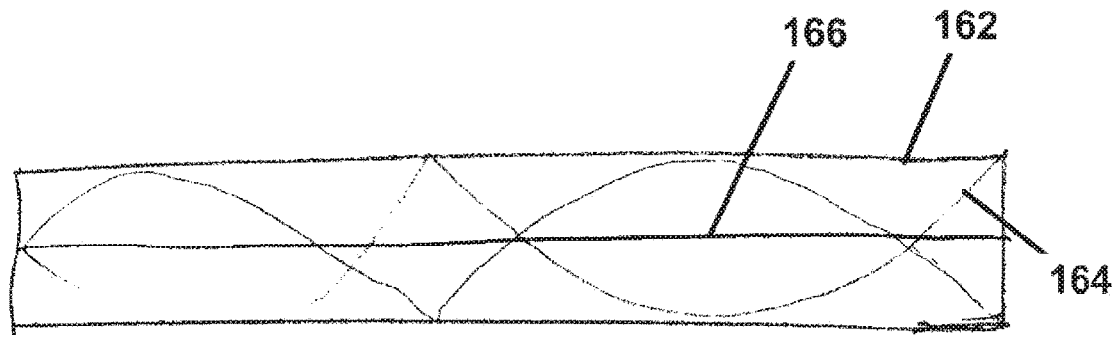

A further variant of an outlet graft 160 is depicted in FIGS. 8a to 8d. The outlet graft 160 comprises a cover 162 and a structure 164, which is made of nitinol and which, as depicted in FIG. 8b, spans the inside of the cover 162 as an endoskeleton. Alternatively, the nitinol structure 164 could also be embodied as an exoskeleton, as depicted in FIG. 8c. Since nitinol is visible for example in an x-ray image, an image as shown in FIG. 8d would be provided in conjunction with the strip 166.

The use of an outlet graft with an x-ray contrast strip during the minimally invasive implantation of a heart pump system, such as a VAD, will now be explained briefly with reference to FIG. 9. FIG. 9 shows an x-ray tomography apparatus 200, which emits x-rays 230 towards a patient 220 lying on an operating table 210. The resultant image of the thorax, calculated by the x-ray tomograph, is output on a monitor 240. On the monitor, the image 250 can be seen, which here shows a schematically depicted ribcage and a heart located therebeneath with an implanted VAD. It can be clearly seen on the graft 260 that the first strip is twisted multiple times. In order to remedy the twisting or rotation, the end of the outlet graft connected to the pump for example should be rotated in a clockwise direction in order to be untwisted. In order to determine this, there is no need for direct visual contact with the graft, and instead merely the x-ray contrast of the strip 270 can be utilised.

Although in all presented exemplary embodiments a first strip running parallel to the longitudinal axis of the cover has been described, in other embodiments a strip running parallel to the longitudinal axis is not necessary. For example, an arbitrarily shaped strip of higher contrast than the material of the cover can be used. Any shapes, for example x-ray contrast strips extending in a meandering form, helically shaped contrast strips, punctiform, circular or cross-shaped contrast strips, circumferential, annular contrast strips arranged parallel to one another along the longitudinal axis of the graft, or other geometries can be used in some exemplary embodiments, alternatively or additionally to a contrast strip.

In some exemplary embodiments the strip is of such a width that a twisting is discernible. For example, the width of the strip can be less than 60°, less than 30°, or less than 15° of the radial circumference. However, the width of the strip is selected in such a way that the strip is clearly visible, in particular in imaging methods.

The invention claimed is:

1. An outlet graft for a blood pump comprising:
   a first end of the outlet graft, the first end configured for connection to the blood pump; and
   a second end of the outlet graft positioned opposite the first end such that a longitudinal axis is formed between the first end and the second end, the second end configured for connection to a blood vessel and a lumen with a closed cover,
   wherein the cover comprises a first strip running parallel to the longitudinal axis and the first strip comprises a material that is of a higher contrast under x-rays than the cover,
   wherein the first end comprises a protective element, the protective element at least partially encasing the cover,
   wherein the protective element comprises a marking oriented parallel to the longitudinal axis and visible under x-ray irradiation, the marking in the form of a strip extending parallel to the first strip, and
   wherein the marking of the protective element serves as a reference for a twisting or rotation of the cover with respect to the protective element indicated by the first strip.

2. The outlet graft according to claim 1, wherein the cover comprises a second strip, running parallel to the longitudinal axis, made of a material of a higher contrast under x-rays than the cover, and the second strip is spaced apart from the first strip.

3. The outlet graft according to claim 2, wherein the cover comprises a third strip that extends helically around the cover, the third strip being made of a material that is of a higher contrast under x-rays than the cover.

4. The outlet graft according to claim 3, wherein the third strip extends helically around the cover from the first end to the second end in a clockwise direction.

5. The outlet graft according to claim 3, wherein the third strip extends helically around the cover from the first end to the second end in an counterclockwise direction.

6. The outlet graft according to claim 1, wherein the cover comprises a polymeric material.

7. The outlet graft according to claim 1, wherein the cover is helically surrounded and reinforced by a plastics material strip.

8. The outlet graft according to claim 1, wherein the first end comprises a connector configured for connection to the blood pump, wherein the connector includes an extension extending in the direction of the second end of the outlet graft.

9. The outlet graft according to claim 8, wherein the extension is in the form of a strip that overlaps the first strip and extends coaxially with the first strip.

10. The outlet graft according to claim 1, wherein the cover includes an endoskeleton, an exoskeleton, or both, made of a shape-memory material.

11. A system, comprising: a blood pump; and an outlet graft, wherein a first end of the outlet graft is connected to an outlet of the blood pump, and a second end of the outlet graft is positioned opposite the first end such that a longitudinal axis is formed between the first end and the second end, the second end connectable to a blood vessel and a lumen with a closed cover,
   wherein the cover comprises a first strip running parallel to the longitudinal axis, the first strip comprising a material that is of higher contrast under x-rays than the cover,
   wherein the first end comprises a protective element, the protective element at least partially encasing the cover,
   wherein the protective element comprises a marking oriented parallel to the longitudinal axis and visible under x-ray irradiation, the marking in the form of a strip extending parallel to the first strip, and wherein the marking of the protective element serves as a reference for a twisting or rotation of the cover with respect to the protective element.

12. The system of claim 11, wherein the blood pump and the outlet graft are configured for use in a hidden implantation of the blood pump.

13. The outlet graft according to claim 6, wherein the polymeric material comprises polytetrafluoroethylene (PTFE).

\* \* \* \* \*